United States Patent
Sloman et al.

(10) Patent No.: US 6,434,428 B1
(45) Date of Patent: Aug. 13, 2002

(54) SYSTEM AND METHOD FOR OPTIMIZING FAR-FIELD R-WAVE SENSING BY SWITCHING ELECTRODE POLARITY DURING ATRIAL CAPTURE VERIFICATION

(75) Inventors: Laurence S. Sloman, West Hollywood; Paul A. Levine, Newhall, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 171 days.

(21) Appl. No.: 09/628,753

(22) Filed: Jul. 31, 2000

Related U.S. Application Data

(63) Continuation-in-part of application No. 09/124,811, filed on Jul. 29, 1998, now Pat. No. 6,101,416.

(51) Int. Cl.⁷ .............................................. A61N 1/37
(52) U.S. Cl. ..................................................... 607/28
(58) Field of Search ............................ 607/28, 13, 27, 607/9; 600/509

(56) References Cited

U.S. PATENT DOCUMENTS

| | | | |
|---|---|---|---|
| 4,549,548 A | 10/1985 | Wittkampt et al. | ... 128/419 PG |
| 4,712,555 A | 12/1987 | Thornander et al. | .. 128/419 PG |
| 4,858,610 A | * 8/1989 | Callaghan et al. | ............. 607/13 |
| 4,940,052 A | 7/1990 | Mann et al. | |
| 4,944,298 A | 7/1990 | Sholder | |
| 5,282,840 A | * 2/1994 | Hudrlik | ........................ 600/547 |
| 5,312,445 A | * 5/1994 | Nappholz et al. | ............... 607/9 |
| 5,330,512 A | * 7/1994 | Hauck et al. | ................... 607/28 |
| 5,458,623 A | 10/1995 | Lu et al. | |
| 5,466,254 A | 11/1995 | Helland | ........................ 607/123 |
| 5,476,486 A | 12/1995 | Lu et al. | |
| 5,573,550 A | 11/1996 | Zadeh et al. | .................... 607/28 |
| 5,683,426 A | * 11/1997 | Greenhut et al. | ............... 607/9 |
| 5,685,315 A | 11/1997 | McClure et al. | ............. 128/708 |
| 5,720,768 A | * 2/1998 | Verboven-Nelissen | .......... 607/9 |
| 5,766,225 A | * 6/1998 | Kramm | ........................... 607/4 |

OTHER PUBLICATIONS

Levine, et al; Assessment of Atril Capture in Commited Atrioventricular Sequential (DVI) Pacing Systems; pp. 616–623.

Pace vol. 6, May–Jun. 19983, Part 1 Levine, et al; Confirmation of Artial Capture and Determination of Atrial Capture Theresholds in DDD Pacing Systems; pp 465–473; Clin. Prog. Pacing and Electrophysiol. 1984, vol. 2, No. 5.

Brandt, et al; Far–Field ORS Complex Sensing via the Atrial Pacemaker Lead. I. Mechanism, Consequences, Differential Diagnosis and Countermeasures in AAI and VDD/DDD Pacing; 1432–1438; Pace vol. 11. Oct. 1988.

Levine; Guidelines to the Foutine Evaluation and Follow–Up of the Implanted Pacing System; pp 19; Siemens Pacesetter; Jan. 1993.

* cited by examiner

*Primary Examiner*—Kennedy Schaetzle

(57) ABSTRACT

An implantable stimulator device provides automatic electrode polarity switching during an atrial capture verification mode. In systems using a bipolar sensing configuration in the atrium, polarity switching will be advantageous in detecting far-field R-waves for verification of capture. This automatic polarity switching feature is programmable and enables or disables automatic switching from bipolar to unipolar sensing at the onset of a far-field interval window and switching again back to bipolar pacing at the end of the far-field interval window.

22 Claims, 6 Drawing Sheets

SYSTEM AND METHOD FOR OPTIMIZING FAR-FIELD R-WAVE SENSING BY SWITCHING ELECTRODE POLARITY DURING ATRIAL CAPTURE VERIFICATION

PRIORITY CLAIM

This application is a continuation-in-part application of copending U.S. application Ser. No. 09/124,811, filed Jul. 29, 1998, now U.S. Pat. No. 6,101,856, entitled "System and Method for Atrial Autocapture in Single-Chamber Pacemaker Modes Using Far-Field Detection," assigned to the same assignee as the present invention, and is incorporated herein by reference in its entirety.

FIELD OF THE INVENTION

The present invention relates in general to implantable cardiac stimulation devices, including bradycardia and anti-tachycardia pacemakers, defibrillators, cardioverters and combinations thereof that are capable of measuring physiological data and parametric data pertaining to implantable medical devices. Particularly, this invention relates to a system and method for automating detection of atrial capture in an implantable cardiac stimulation device using far-field signal detection. More specifically, this invention provides for the automatic optimization of far-field R-wave sensing by switching electrode polarity during atrial capture verification.

BACKGROUND OF THE INVENTION

Implantable medical devices, such as pacemakers, defibrillators, and cardioverters (collectively referred to herein as implantable cardiac stimulating devices), are designed to monitor and stimulate the heart of a patient that suffers from a cardiac arrhythmia. Using leads connected to a patient's heart, these devices typically stimulate the cardiac muscles by delivering electrical pulses in response to measured cardiac events that are indicative of a cardiac arrhythmia. Properly administered therapeutic electrical pulses often successfully reestablish or maintain the heart's regular rhythm.

Implantable cardiac stimulating devices can treat a wide range of cardiac arrhythmias by using a series of adjustable parameters to alter the energy, shape, location, and frequency of the therapeutic pulses. The adjustable parameters are usually defined in a computer program stored in a memory of the implantable device. The program (which is responsible for the operation of the implantable device) can be defined or altered telemetrically by a medical practitioner using an external implantable device programmer.

Modern programmable pacemakers, the most commonly used implantable devices, are generally of two types: (1) single-chamber pacemakers, and (2) dual-chamber pacemakers. In a single-chamber pacemaker, the pacemaker provides stimulation pulses to, and senses cardiac activity within, a single-chamber of the heart (e.g. either the right ventricle or the right atrium). In a dual-chamber pacemaker, the pacemaker provides stimulation pulses to, and senses cardiac activity within, two chambers of the heart (e.g. both the right atrium and the right ventricle). The left atrium and left ventricle can also be paced, provided that suitable electrical contacts are effected therewith.

In general, both single and dual-chamber pacemakers are classified by type according to a three letter code. In this code, the first letter identifies the chamber of the heart that is paced (i.e. the chamber where a stimulation pulse is delivered)—with a "V" indicating the ventricle, an "A" indicating the atrium, and a "D" (dual) indicating both the atrium and ventricle. The second letter of the code identifies the chamber where cardiac activity is sensed, using the same letters to identify the atrium or ventricle or both, and where an "O" indicates that no sensing takes place.

The third letter of the code identifies the action or response that is taken by the pacemaker. In general, three types of action or responses are recognized: (1) an Inhibiting ("I") response, where a stimulation pulse is delivered to the designated chamber after a set period of time unless cardiac activity is sensed during that time, in which case the stimulation pulse is inhibited; (2) a Trigger ("T") response, where a stimulation pulse is delivered to the designated chamber of the heart a prescribed period after a sensed event; or (3) a Dual ("D") response, where both the Inhibiting mode and Trigger mode are evoked, inhibiting in one chamber of the heart and triggering in the other.

A fourth letter, "R", is sometimes added to the code to signify that the particular mode identified by the three letter code is rate-responsive, where the pacing rate may be adjusted automatically by the pacemaker based on one or more physiological factors such as blood oxygen level or the patient's activity level.

Modem pacemakers also have a great number of adjustable parameters that must be tailored to a particular patient's therapeutic needs. One adjustable parameter of particular importance in pacemakers is the pacemaker's stimulation energy. "Capture" is defined as a cardiac response to a pacemaker stimulation pulse. When a pacemaker stimulation pulse stimulates either a heart atrium or a heart ventricle during an appropriate portion of a cardiac cycle, it is desirable to have the heart properly respond to the stimulus provided. Every patient has a "capture threshold" which is generally defined as the minimum amount of stimulation energy necessary to effect capture. Capture should be achieved at the lowest possible energy setting yet provide enough of a safety margin so that, should a patient's threshold increase, the output of an implantable pacemaker, i.e. the stimulation energy, will still be sufficient to maintain capture. Dual-chamber pacemakers may have differing atrial and ventricular stimulation energy that correspond to atrial and ventricular capture thresholds, respectively.

The earliest pacemakers had a predetermined and unchangeable stimulation energy, which proved to be problematic because the capture threshold is not a static value and may be affected by a variety of physiological and other factors. For example, certain cardiac medications may temporarily raise or lower the threshold from its normal value. In another example, fibrous tissue that forms around pacemaker lead heads within several months after implantation may raise the capture threshold.

As a result, some patients eventually suffered from loss of capture as their pacemakers were unable to adjust the pre-set stimulation energy to match the changed capture thresholds. One attempted solution was to set the level of stimulation pulses fairly high so as to avoid loss of capture due to a change in the capture threshold. However, this approach resulted in some discomfort to patients who were forced to endure unnecessarily high levels of cardiac stimulation. Furthermore, such stimulation pulses consumed extra battery resources, thus shortening the useful life of the pacemaker.

When programmable pacemakers were developed, the stimulation energy was implemented as an adjustable parameter that could be set or changed by a medical practitioner. Typically, such adjustments were effected by the medical practitioner using an external programmer capable of communication with an implanted pacemaker via a magnet applied to a patient's chest or via telemetry. The particular setting for the pacemaker's stimulation energy was usually derived from the results of extensive physiological tests performed by the medical practitioner to determine the patient's capture threshold, from the patient's medical history, and from a listing of the patient's medications. While the adjustable pacing energy feature proved to be superior to the previously known fixed energy, some significant problems remained unsolved. In particular, when a patient's capture threshold changed, the patient was forced to visit the medical practitioner to adjust the pacing energy accordingly.

To address this pressing problem, pacemaker manufacturers have developed advanced pacemakers that are capable of determining a patient's capture threshold and automatically adjusting the stimulation pulses to a level just above that which is needed to maintain capture. This approach, called "autocapture", improves the patient's comfort, reduces the necessity of unscheduled visits to the medical practitioner, and greatly increases the pacemakers battery life by conserving the energy used to generate stimulation pulses.

However, many of these advanced pacemakers require additional circuitry and/or special sensors that must be dedicated to capture verification. This requirement increases the complexity of the pacemaker system and reduces the precious space available within a pacemaker's casing, and also increases the pacemaker's cost. As a result, pacemaker manufacturers have attempted to develop automatic capture verification techniques that may be implemented in a typical programmable pacemaker without requiring additional circuitry or special dedicated sensors.

A common technique used to determine whether capture has been effected is monitoring the patient's cardiac activity and searching for the presence of an "evoked response" following a stimulation pulse. The evoked response is the response of the heart to application of a stimulation pulse. The patient's heart activity is typically monitored by the pacemaker by keeping track of the stimulation pulses delivered to the heart and examining, through the leads connected to the heart, electrical signals that are manifest concurrent with depolarization or contraction of muscle tissue (myocardial tissue) of the heart. The contraction of atrial muscle tissue is evidenced by generation of a P-wave, while the contraction of ventricular muscle tissue is evidenced by generation of an R-wave (sometimes referred to as the "QRS" complex).

When capture occurs, the evoked response is an intracardiac P-wave or R-wave that indicates contraction of the respective cardiac tissue in response to the applied stimulation pulse. For example, using such an evoked response technique, if a stimulation pulse is applied to the atrium (hereinafter referred to as an A-pulse), any response sensed by atrial sensing circuits of the pacemaker immediately following application of the A-pulse is presumed to be an evoked response that evidences capture of the atria.

However, it is for several reasons very difficult to detect a true evoked response. First, because the atrial evoked response is a relatively small signal, it may be obscured by a high energy A-pulse and therefore difficult to detect and identify. Second, the signal sensed by the pacemaker's sensing circuitry immediately following the application of a stimulation pulse may be not an evoked response but noise—either electrical noise caused, for example, by electromagnetic interference, or myocardial noise caused by random myocardial or other muscle contraction.

Another signal that interferes with the detection of an evoked response, and potentially the most difficult for which to compensate because it is usually present in varying degrees, is lead polarization. A lead/tissue interface is that point at which an electrode of the pacemaker lead contacts the cardiac tissue. Lead polarization is commonly caused by electrochemical reactions that occur at the lead/tissue interface due to application of an electrical stimulation pulse, such as an A-pulse, across the interface. Unfortunately, because the evoked response is sensed through the same lead electrodes through which the stimulation pulses are delivered, the resulting polarization signal, also referred to herein as an "afterpotential", formed at the electrode can corrupt the evoked response that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation energy and other variables, many of which are continually changing over time. In each of the above cases, the result may be a false positive detection of an evoked response. Such an error leads to a false capture indication, which in turn leads to missed heartbeats—a highly undesirable and potentially life-threatening situation. Another problem results from a failure by the pacemaker to detect an evoked response that has actually occurred. In that case, a loss of capture is indicated when capture is in fact present—also an undesirable situation that will cause the pacemaker to unnecessarily invoke the pacing energy determination function in a chamber of the heart.

Automatic pacing energy determination is only invoked by the pacemaker when loss of atrial or ventricular capture is detected. An exemplary prior art automatic atrial pacing energy determination procedure is performed as follows. When loss of atrial capture is detected, the pacemaker increases the A-pulse output level to a relatively high predetermined testing level at which capture is certain to occur, and thereafter decrements the output level until atrial capture is lost. The atrial pacing energy is then set to a level slightly above the lowest output level at which atrial capture was attained. Thus, atrial capture verification is of utmost importance in proper determination of the atrial pacing energy.

When an atrial stimulation pulse is properly captured in the atrium, a subsequent ventricular contraction results in an R-wave which may be sensed through an atrial lead, in patients with intact atriovenricular ("AV") conduction, as a "far-field" signal. The far-field R-wave confirms successful atrial capture because the ventricular contraction only occurs after a properly captured atrial stimulation pulse. Previously known pacemakers have ignored this useful phenomenon because previously known single-chamber atrial pacemakers and dual-chamber pacemakers programmed to operate in an atrial mode purposefully do not sense ventricular activity through the atrial lead for a particular period of time (i.e. the "refractory" period) after delivery of the atrial stimulation pulse. Furthermore, the polarization signal formed at the atrial lead electrode may obscure and/or distort the far-field R-wave signal, even if it were sensed.

A further difficulty in achieving optimal sensing of desired signals is selecting the most appropriate electrode polarity configuration. Typically, either a unipolar or a bipolar configuration is used for pacing and sensing in the heart chambers.

In a unipolar configuration, one electrode is positioned at, or near the distal end of the lead body, in contact with the heart tissue. A ground or "indifferent" electrode, commonly the pacemaker housing or can, is placed some distance away. In a bipolar configuration, two electrodes are placed in close proximity to each other at the distal end of the lead body, typically in a "tip" and "ring" configuration, such that both electrodes have contact with the heart tissue.

Determining the ideal polarity configuration remains enigmatic. Medical practitioners tend to have personal preferences and patient variability may make one configuration more successful than another for unknown reasons. Generally, bipolar configurations require less pacing energy, and are less prone to noise or crosstalk than unipolar configurations. Crosstalk is defined as the sensing of signals occurring in other heart chambers, sensing output from other channels in a multi-chamber device, or from other devices when more than one stimulating device is implanted. Noise signals can occur when myopotentials are detected by the lead system. Bipolar pacing is preferred over unipolar pacing when extraneous stimulation of skeletal muscle tissue occurs or device pocket infection occurs. However, unipolar pacing and sensing also present certain advantages. Compared to bipolar configurations, greater sensitivity is achieved and polarization effects are lessened due to a typically large indifferent electrode. Sensing in the atrium may be better achieved by unipolar sensing configurations since P-wave signals are relatively small in amplitude. Particular tasks in detecting sensed events in response to a stimulation pulse may also be better performed in unipolar systems.

New combinations of electrodes are now available, widening the selection a physician has to choose from in deciding which configuration is the most suitable. For example, unipolar systems may be selectively programmable as using a lead tip electrode and pacemaker can or a lead ring electrode and pacemaker can. Combipolar systems using the lead tip electrodes or lead ring electrodes of two different leads, that is "tip-to-tip" or "ring-to-ring" configurations, are also possible in dual chamber devices.

In light of these new combinations and the complexity of pacing systems which may be sensing and pacing in up to four heart chambers, it is desirable to allow selection of the electrode polarity that works best in both minimizing pacing energy and accurately sensing intrinsic as well as evoked responses following stimulation pulses.

Methods of automatically switching electrode polarity for attaining optimal sensing or pacing configurations for a given task or under specific circumstances are known in the field. Reference is made to U.S. Pat. No. 4,549,548 to Wittkampf et al.

Despite these methods for improving the sensing capabilities of a pacemaker, there remains an unsatisfied need for accurately verifying atrial capture based on the sensed signals. It would thus be desirable to provide a system and method for enabling the pacemaker to automatically and accurately perform atrial capture verification by sensing and identifying a far-field R-wave that occurs only after delivery by the pacemaker of a successfully captured atrial stimulation pulse. It would also be desirable to provide a system and method for reducing the negative effect of polarization and noise on capture verification by automatically isolating such negative effects from the identified far-field R-wave signal. It would further be desirable to allow automatic electrode polarity configuration switching during atrial capture verification such that sensing of far-field R-waves is optimized.

It would further be desirable to enable the pacemaker to perform atrial capture verification without requiring dedicated circuitry and/or special sensors.

SUMMARY OF THE INVENTION

The disadvantages and limitations discussed above are overcome by the present invention. In accordance with the invention, a system and method are provided for automating verification of proper atrial capture of pacing pulses generated by a patient's implantable cardiac stimulation device by sensing and identifying a far-field ventricular signal resulting from a ventricular contraction that follows a successfully captured atrial stimulation pulse. The system and method of the present invention compensate for effects of polarization and noise on the identified far-field signal and do not require use of special dedicated circuitry or special sensors to implement the automated procedure. All of the aforesaid advantages and features are achieved without incurring any substantial relative disadvantage.

The present invention provides an implantable medical device (hereinafter "pacemaker") equipped with cardiac data acquisition capabilities. A preferred embodiment of the pacemaker of the present invention includes a control system for controlling the operation of the pacemaker, a set of leads for receiving atrial and ventricular signals and for delivering atrial and ventricular stimulation pulses, a set of sense amplifiers for sensing and amplifying the atrial and ventricular signals, a sampler, such as an A/D converter, for sampling atrial and/or ventricular signals, and pulse generators for generating the atrial and ventricular stimulation pulses. In addition, the pacemaker includes memory for storing operational parameters for the control system, such as atrial or ventricular signal sampling parameters, and atrial or ventricular signal samples. The pacemaker also includes a telemetry circuit for communicating with an external programmer.

In a preferred embodiment of the invention, the pacemaker control system periodically performs an atrial capture verification test and, when necessary, an atrial pacing threshold assessment test, which performs an assessment of the stimulation energy in the atrial chamber of the patient's heart. The frequency with which these tests are performed are preferably programmable parameters set by the medical practitioner using an external programmer when the patient is examined during an office visit or remotely via a telecommunication link. The appropriate testing frequency parameter will vary from patient to patient and depend on a number of physiologic and other factors. For example, if a patient is on a cardiac medication regimen, the patient's atrial capture threshold may fluctuate, thus requiring relatively frequent testing and adjustment of the atrial stimulation energy. Preferably the system and method of the present invention are implemented in a pacemaker operating in an atrial mode such as AAI, AOO or AAT.

In a first embodiment of the invention, the pacemaker delivers an atrial stimulation pulse and then samples a resulting far-field ventricular signal during a predetermined far-field interval window that is centered at the expiration of a predetermined window delay. The pacemaker then compares the far-field signal sample to a predetermined far-field signal recognition template to verify whether the far-field signal sample morphology corresponds to a far-field R-wave that is expected to follow a successfully captured atrial stimulation pulse. If the far-field signal sample is approximately equal to the far-field signal recognition template, then atrial capture is deemed verified. Otherwise, the pacemaker performs an atrial stimulation energy determination procedure. This embodiment of the invention is preferably implemented in a pacemaker that is equipped with special electrodes and/or circuitry for reducing or eliminating noise and polarization signals that occur after delivery of atrial stimulation pulses.

In a second embodiment of the invention, the pacemaker delivers an atrial stimulation pulse, samples a response signal in the atrium, and then samples a resulting far-field ventricular signal during a predetermined far-field interval window that is centered at the expiration of a predetermined window delay. The response sample is then compared to the far-field sample and is compared to a predetermined far-field signal recognition template. If the sample is approximately equal to the far-field signal recognition template, then atrial capture is deemed verified. Otherwise, the pacemaker performs an atrial stimulation energy determination procedure.

Preferably, the window delay and the far-field signal recognition template are automatically determined by the pacemaker after initial implantation, and updated at other times as necessary or appropriate, as for example under the direction of the medical practitioner during a follow-up visit. In accordance with the invention, the pacemaker performs an AR conduction test to determine a conduction time and then stores the conduction time in memory. The pacemaker then delivers an atrial stimulation pulse, samples a response signal in the atrium, stores the response sample in memory, then samples a resulting far-field ventricular signal after a delay approximately equal to the conduction time and stores the far-field sample in memory.

When a predetermined number of samples and conduction times are thus acquired, the pacemaker averages each set of samples and subtracts the response sample average from the far-field signal sample average to produce a far-field signal recognition template, which is then stored in memory. The pacemaker also averages the conduction times to determine an average window delay, centers the predefined far-field interval window at the average conduction time (window delay) and stores the position of the far-field interval window in memory.

Alternately, the window delay and the far-field signal recognition template may be predefined by the medical practitioner and stored in the pacemaker memory along with the far-field interval window.

In an alternative embodiment, the present invention provides for automatic electrode polarity switching during the atrial capture verification method. In systems using a bipolar sensing configuration in the atrium, far-field signals may or may not be detected due to the characteristically low amplitude of these signals. In such bipolar systems, polarity switching, that is switching from bipolar sensing to unipolar sensing, at the onset of a far-field interval window will be advantageous in detecting far-field R-waves for verification of capture. Thus, an optional programmable feature is provided that will enable or disable automatic switching to unipolar sensing at the onset of the far-field interval window and switching again back to bipolar pacing at the end of the far-field interval window.

The system and method of the present invention thus automatically verify atrial capture and, when necessary, automatically determine a proper atrial stimulation energy of the patient's pacemaker, without requiring dedicated or special circuitry and/or sensors.

BRIEF DESCRIPTION OF THE DRAWINGS

The above and further features, advantages and benefits of the invention will become apparent in the following description taken in conjunction with the following drawings. It is to be understood that the foregoing general description and the following detailed description are exemplary and explanatory but are not intended to be restrictive of the invention. The accompanying drawings, which are incorporated in and constitute a part of this disclosure, illustrate several embodiments of the invention and, together with the description, serve to explain the principles of the invention in general terms. Like numerals refer to like parts throughout the disclosure.

DETAILED DESCRIPTION OF THE INVENTION

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

The system and method of the present invention utilize a pacemaker's normal sensing and control circuitry to perform automatic atrial capture verification and, when necessary, an atrial stimulation energy determination test.

The system and method of the present invention are intended for use in a single-chamber atrial pacemaker, or in a dual-chamber pacemaker programmed to operate in a single-chamber atrial pacing mode such as AOO, AAI, or AAT, and implanted in a patient who has intact atrioventricular ("AV") conduction. While the system and method of the invention are described by way of illustrative examples with specific reference to a dual-chamber pacemaker, it will thus be understood that the invention may instead be applied to a single-chamber atrial pacemaker, in which a sensing/pacing lead is connected to the atrial chamber of the heart, without departing from the spirit of the invention.

Figure 1:
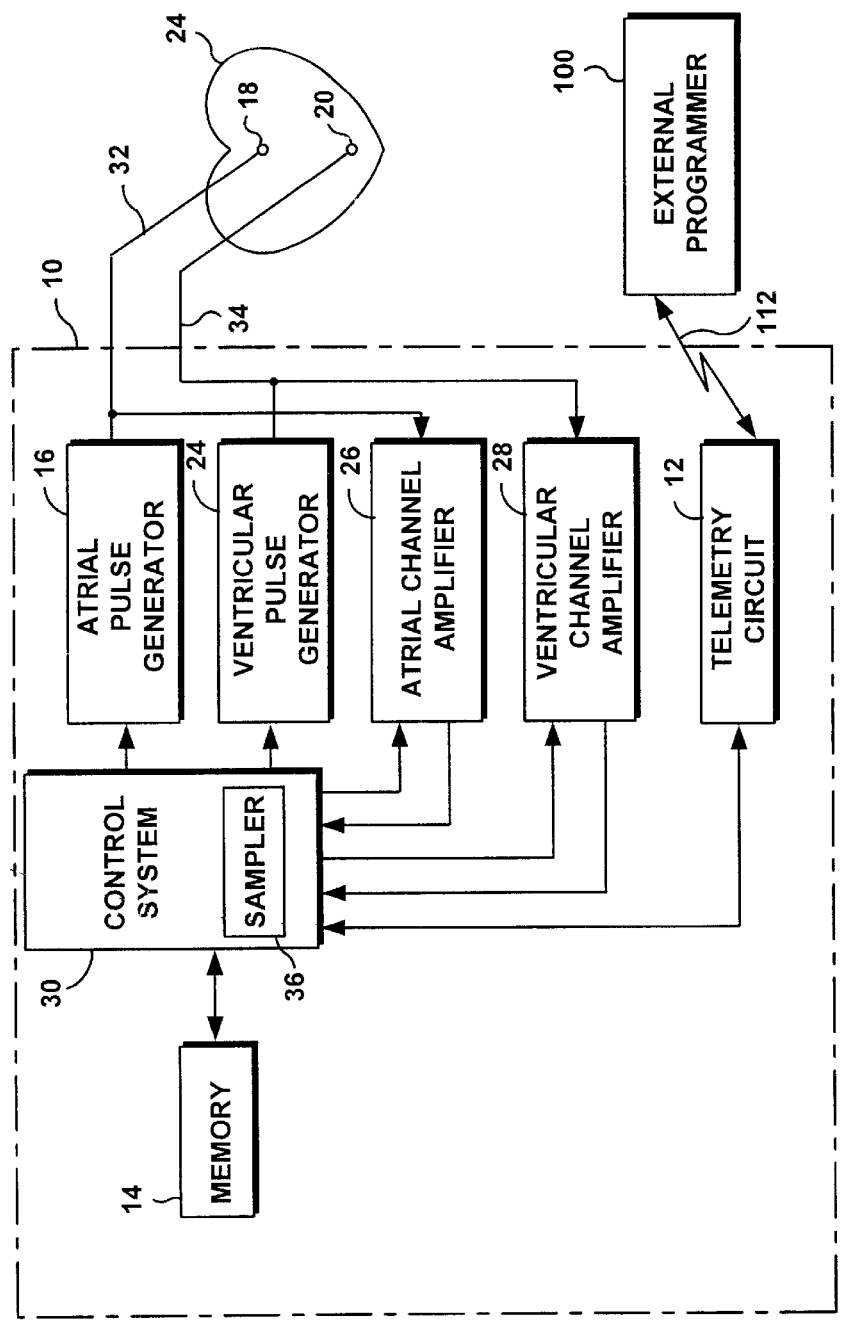
FIG. 1 is a block diagram of a dual-chamber pacemaker in accordance with the principles of the present invention.

A pacemaker 10 in accordance with the invention is shown in FIG. 1. The pacemaker 10 is coupled to a patient's heart 24 by way of leads 32 and 34, the lead 32 having an electrode 18 which is in contact with one of the atria of the heart 24, and the lead 34 having an electrode 20 which is in contact with one of the ventricles. The lead 32 carries stimulating pulses to the electrode 18 from an atrial pulse generator 16, while the lead 34 carries stimulating pulses to the electrode 20 from a ventricular pulse generator 22. In addition, electrical signals from the atria are carried from the electrode 18, through the lead 32, to the input terminal of an atrial channel amplifier 26. Electrical signals from the ventricles are carried from the electrode 20, through the lead 34 to the input terminal of a ventricular channel amplifier 28.

Operatively controlling the dual-chamber pacemaker 10 is a control system 30. The control system 30 is preferably a microprocessor-based system such for example as that disclosed in commonly-assigned U.S. Pat. No. 4,940,052 of Mann, which is incorporated herein by reference in its entirety. The control system 30 may also be a state logic-based system such for example as that disclosed in commonly assigned U.S. Pat. No. 4,944,298 of Sholder, which is also incorporated herein by reference in its entirety. The control system 30 includes a real-time clock (not shown) providing timing functionality for monitoring cardiac events and for timing the application of therapeutic pulses by the pulse generators 16 and 24. The control system 30 also includes a sampler 36, such as an A/D converter, for generating digital signals representative of cardiac activity by sampling the atrial and/or ventricular cardiac signals acquired by the respective amplifiers 26 and 28. Alternately, the sampler 36 may be implemented separately from the control system 30 and connected directly to the amplifiers 26 and 28.

The pacemaker 10 also includes a memory 14 which is coupled to the control system 30. The memory 14 allows certain control parameters used by the control system 30 in controlling the operation of the pacemaker 10 to be programmably stored and modified, as required, to customize the operation of the pacemaker 10 to suit the needs of a particular patient. In particular, parameters regulating the operation of the sampler 36 are stored in the memory 14. In addition, samples acquired by the sampler 36 may be stored in the memory 14 for later analysis by the control system 30.

The control system 30 receives the output signals from the atrial channel amplifier 26. Similarly, the control system 30 also receives the output signals from the ventricular channel amplifier 28. These various output signals are generated each time that an atrial event (e.g. a P-wave) or a ventricular event (e.g. an R-wave) is sensed within the heart 24.

The control system 30 also generates an atrial trigger signal that is sent to the atrial pulse generator 16, and a ventricular trigger signal that is sent to the ventricular pulse generator 22. These trigger signals are generated each time that a stimulation pulse is to be generated by one of the pulse generators 16 or 22. The atrial stimulation pulse is referred to simply as the "A-pulse", and the ventricular stimulation pulse is referred to as the "V-pulse". The characteristics of these stimulation pulses are determined by pacing energy settings that are among the parameters stored in the memory 14. The control system 30 may also be programmed to operate the pacemaker 10 in a variety of pacing and sensing modes. Preferably, the control system 30 is programmed to a single-chamber atrial mode such as AOO, AAI, or AAT.

A telemetry circuit 12 is further included in the pacemaker 10 and connected to the control system 30. The telemetry circuit 12 may be selectively coupled to an external programmer 100 by means of an appropriate communication link 112, such as an electromagnetic telemetry link or a remote communication link such as a pair of modems interconnected via a telecommunications link and equipped with telemetry capabilities.

The operation of the pacemaker 10 is generally controlled by a control program stored in the memory 14 and executed by the control system 30. This control program typically consists of multiple integrated program modules, with each module bearing responsibility for controlling one or more functions of the pacemaker 10. For example, one program module may control the delivery of stimulating pulses to the heart 24, while another may control the verification of atrial capture and atrial pacing energy determination. In effect, each program module is a control program dedicated to a specific function or set of functions of the pacemaker 10.

Figure 5:
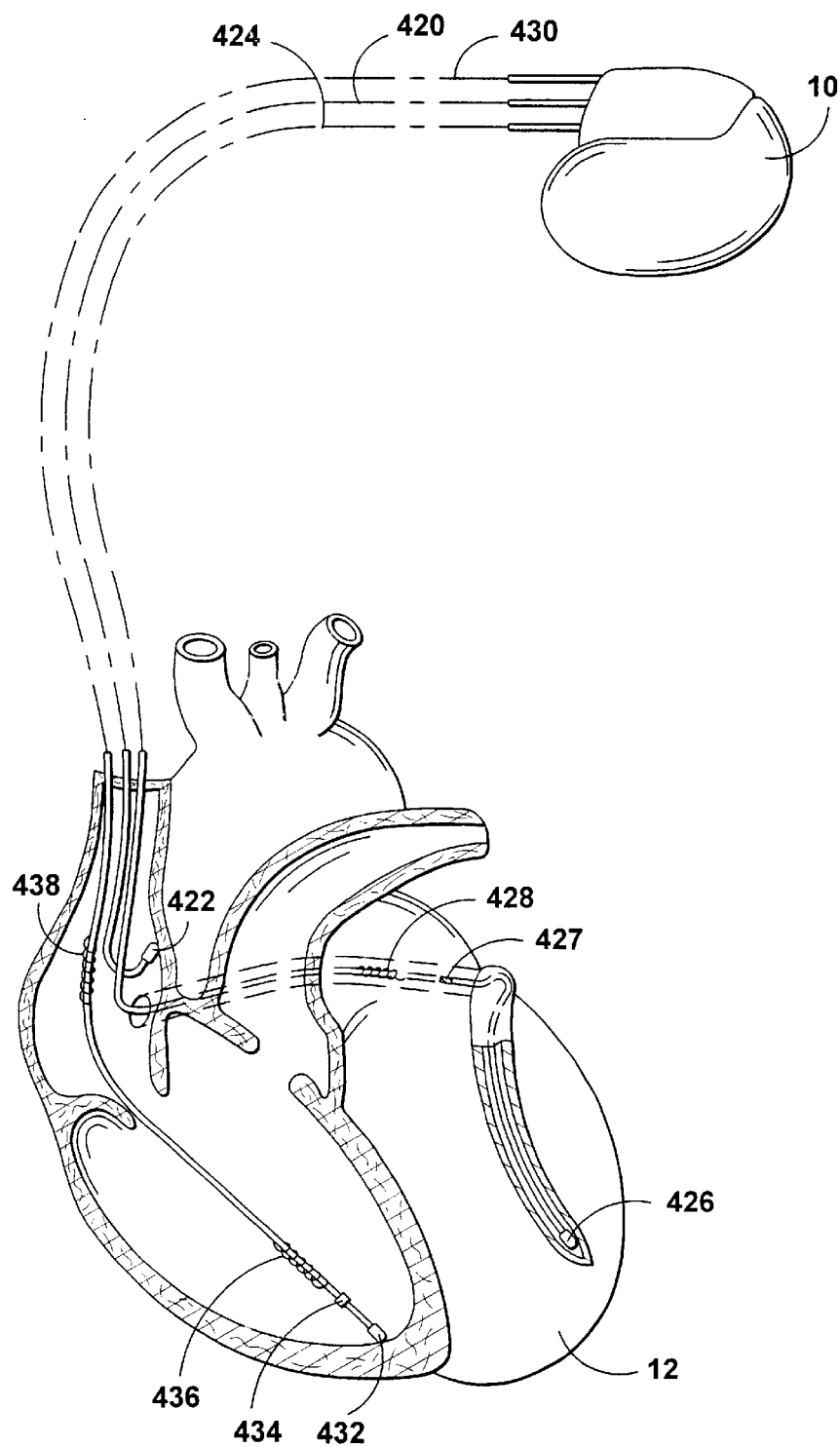
FIG. 5 is a simplified, party cutaway view illustrating an alternative implantable stimulation device in electrical communication with at least three leads implanted into a patient's heart for delivering multi-chamber stimulation and shock therapy.
Figure 6:
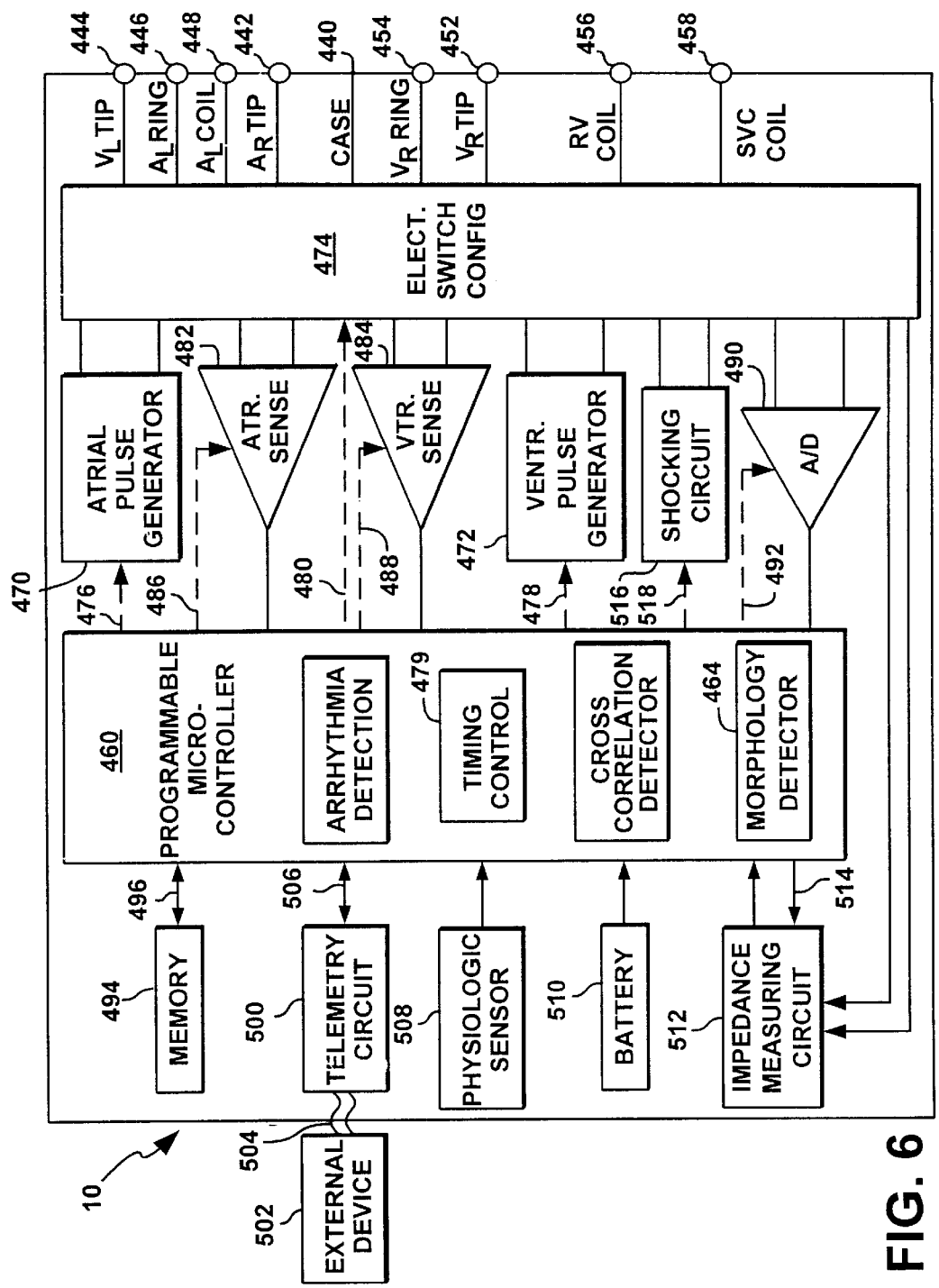
FIG. 6 is a functional block diagram of the multi-chamber implantable stimulation device of FIG. 5, illustrating the basic elements that provide cardioversion, defibrillation and pacing stimulation in four chambers of the heart.

In the alternative embodiment of FIGS. 5 and 6, the stimulation device 10 contains switch circuitry or bank 474 which is comprised of a plurality of switches for connecting the desired electrodes to the appropriate I/O circuits, thereby providing complete electrode programmability. Accordingly, the switch bank 474, in response to a control signal 480 from a microcontroller 460, determines the polarity of the stimulation pulses (e.g. unipolar, bipolar, combipolar, etc.) by selectively closing the appropriate combination of switches. Likewise, the switch bank 474 determines the "sensing polarity" of the cardiac signal by selectively closing the appropriate switches. In this way, the clinician may program the sensing polarity independent of the stimulation polarity.

Figure 2:
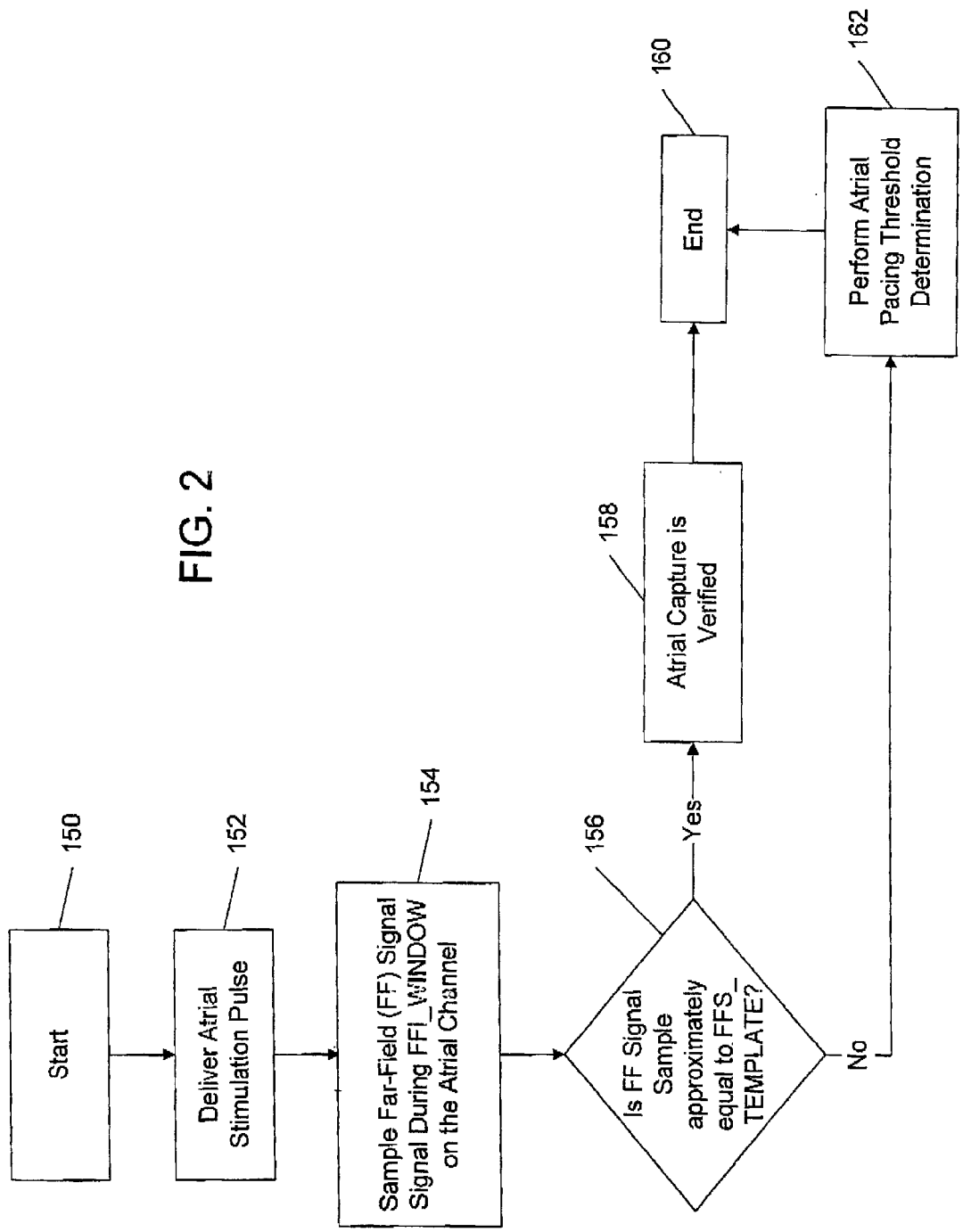
FIG. 2 is a logic flow diagram of a first embodiment of an automatic atrial capture verification and atrial stimulation energy determination control program executed by the control system of the pacemaker of FIG. 1, in accordance with the principles of the present invention.

FIG. 2 depicts a logic flow diagram representing a first embodiment of a control program for controlling the atrial capture verification and atrial pacing energy determination procedure executed by the control system 30 in accordance with the present invention. The control program of FIG. 2 is preferably used in a pacemaker that is equipped with special electrodes and/or circuitry for reducing or eliminating noise and polarization signals that occur after delivery of stimulation pulses. Preferably, the control system 30 periodically invokes the control program to perform the capture verification test and, when necessary or appropriate, the atrial pacing energy assessment test in the atrial chamber of the heart 24. The frequency with which these tests are to be performed are preferably programmable parameters set by the medical practitioner using the external programmer 100 when the patient is examined during an office visit or remotely via the communication link 112. The appropriate testing frequency parameter will vary from patient to patient and depend on a number of physiologic and other factors. For example, if a patient is on a cardiac medication regimen, the patient's atrial capture threshold may fluctuate, thus requiring relatively frequent testing and adjustment of the atrial pacing energy.

After the atrial capture verification test begins at a step 150, the control system 30 at a step 152 causes the atrial pulse generator 16 to deliver a stimulation pulse to the atrial chamber. Typically, the atrial stimulation pulse triggers a subsequent ventricular contraction resulting in a ventricular R-wave that is sensed by the atrial sense amplifier 26 through the atrial lead 32 as a far-field signal. The lack of a ventricular contraction subsequent to the delivery of the atrial stimulation pulse commonly indicates absence of atrial capture.

At a step 154, the system 30 samples the far-field signal via the sampler 36 during a predefined far-field interval window ("FFI_WINDOW"). The FFI_WINDOW is preferably "centered" at the expiration of an expected window delay between the delivery of the atrial stimulation pulse and generation of the far-field signal. For example, if the expected window delay is 20 ms, and the FFI_WINDOW is defined to be 10 ms, then the FFI_WINDOW will begin 15 ms after delivery of the atrial stimulation pulse, and will end 10 ms later (i.e. 25 ms after the delivery of the pulse). This expected window delay is approximately equal to AV conduction time. While it is expected that the far-field signal will occur at approximately the expiration of the window delay, it is possible that for a variety of reasons the far-field signal actually occurs shortly before or shortly after the delay. The purpose of the FFI_WINDOW is thus to provide an opportunity for the control system 30 to sense a far-field signal that does not occur exactly after the expected window delay. A control program module for automatically determining the expected window delay and centering the FFI_WINDOW at the expected window delay is described below in connection with FIG. 4.

At a test 156, the control system 30 compares the far-field signal sample obtained at the step 154 with a far-field signal recognition template ("FFS_TEMPLATE") stored in the memory 14 to determine whether the far-field signal sample is approximately equal to the FFS_TEMPLATE. The FFS_TEMPLATE is preferably representative of a morphology of a typical far-field signal that occurs in the patient's heart 24. The FFS_TEMPLATE may be supplied by the medical practitioner using the programmer 100 or, preferably, may be automatically determined by the control system 30. The control program module described below in connection with FIG. 4 demonstrates an advantageous and preferred technique for automatically determining the FFS_TEMPLATE.

If it is determined at the test 156 that the far-field signal sample is approximately equal to the FFS_TEMPLATE, then at a step 158 atrial capture is deemed to have been verified, and the control program ends at a step 162. If, on the other hand, the far-field signal sample is not approximately equal to the FFS_TEMPLATE, then at a step 162 the control system 30 performs an atrial pacing energy determination procedure. Various advantageous and appropriate atrial pacing energy determination procedures are well known in the art and will not therefore be described herein.

In an alternative embodiment, to be applied particularly in bipolar pacing systems, a control program for automatically switching the electrode polarity is executed by the control system 30 upon the initiation of the atrial capture verification test described earlier in connection with FIG. 2. A bipolar sensing configuration may not allow accurate far-field signal detection, and therefore automatic switching from bipolar to unipolar sensing is expected to improve the performance of the atrial capture verification test.

Automatic electrode polarity switching would be triggered by control system 30 (or by the microcontroller 460 of the embodiment of FIG. 6), to occur near the onset and termination of the FFI_WINDOW. Thus, at the start of the FFI_WINDOW, electrode polarity would be switched to a unipolar configuration, and at the end of the FFI_WINDOW, electrode polarity would be switched back to a bipolar configuration for the duration of the pacing (or stimulation) cycle.

Automatic electrode polarity switching is preferably a programmable feature, with the automatic switching either enabled or disabled and, if enabled, the electrode configuration to be applied during the atrial capture verification test is also designated.

Depending on the overall pacing system and electrode configuration used, more than one unipolar or other polarity configuration may be possible. The optimal sensing configuration for far-field signal detection would thus be determined by the medical practitioner during an office visit. The electrode configuration that results in consistently accurate far-field signal detection would be selected based on observation of the far-field signal during the different programmable electrode configurations available. This sensing electrode configuration would then be applied during the collection of the FFS_TEMPLATE, as will be described later in connection with FIG. 4, and during the atrial capture test of FIG. 2.

Figure 3:
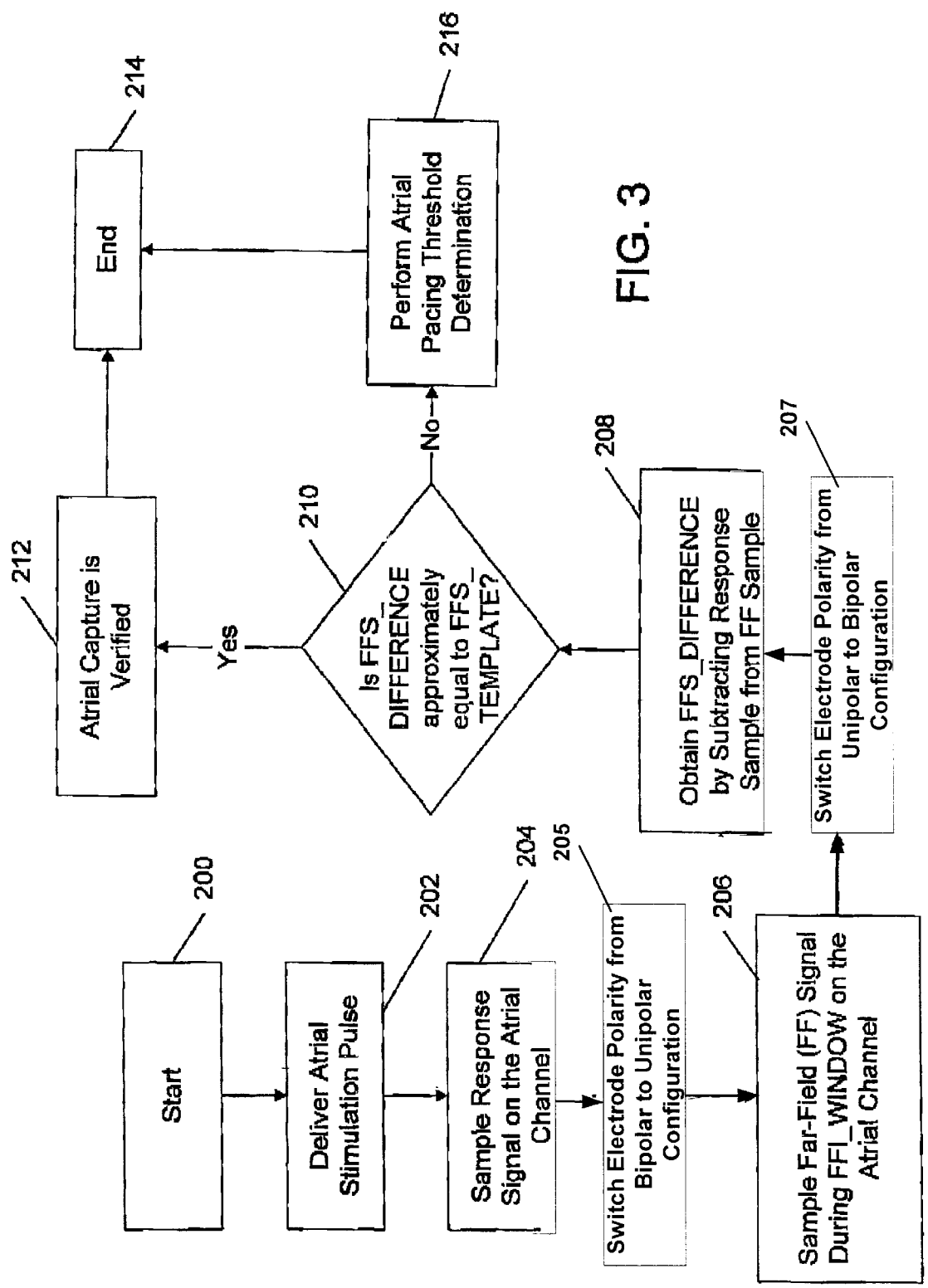
FIG. 3 is a logic flow diagram of another embodiment of an automatic atrial capture verification and atrial pacing threshold determination control program executed by the control system of the pacemaker of FIG. 1, in accordance with the principles of the present invention.

FIG. 3 depicts a logic flow diagram representing a second embodiment of a control program for controlling the atrial capture verification and atrial pacing energy determination procedure executed by the control system 30 in accordance with the present invention. Unlike the control program of FIG. 2, the control program of FIG. 3 may be used in a pacemaker that is not equipped with special electrodes and/or circuitry for reducing or eliminating polarization signals that occur after delivery of stimulation pulses. As with the previously described control program of FIG. 2, the control system 30 periodically invokes the alternative control program of FIG. 3 to perform the capture verification test and, when necessary, the atrial pacing energy assessment test in the atrial chamber of the heart 24.

After the atrial capture verification test of FIG. 3 begins at a step 200, the control system 30 at a step 202 causes the atrial pulse generator 16 to deliver a stimulation pulse to the atrial chamber. When delivered, the atrial stimulation pulse triggers a response signal in the atrial chamber that may consist of an evoked response representative of an atrial contraction combined with a polarization signal and other noise. Typically, the atrial stimulation pulse also triggers a subsequent ventricular contraction resulting in a ventricular R-wave that is sensed by the atrial channel amplifier 26 through the atrial lead 32 as a far-field signal. The lack of a ventricular contraction subsequent to the delivery of the atrial stimulation pulse commonly indicates absence of atrial capture.

At a step 204, the control system 30 samples the response signal via the sampler 36. To improve accurate sensing of the far-field signal, automatic electrode polarity switching may be invoked at a step 205, as described above. At the onset of the FFI_WINDOW, the switching circuitry controlled by control system 30 automatically switches the electrode polarity from the preferred stimulation polarity configuration to the preferred capture sensing polarity such that the far-field signal sampled at step 206 is more distinct. At a step 206, also samples the far-field signal via the sampler 36 during a predefined FFI_WINDOW. As was previously described in connection with FIG. 2, the FFI_WINDOW is preferably "centered" at the expiration of the expected window delay between the delivery of the atrial stimulation pulse and generation of the far-field signal. At the end of the FFI_WINDOW, at a step 207, the switching circuitry automatically switches the electrode polarity from the preferred capture sensing polarity to the preferred stimulation polarity.

At a step 208, the control system 30 obtains a far-field signal difference ("FFS_DIFFERENCE") by subtracting the response sample obtained at the step 204 from the far-field signal sample obtained at the step 206. The FFS_DIFFERENCE is representative of a true far-field signal without the distorting effects of an overlapping atrial response, such as polarization. At a test 210, the control system 30 compares the FFS_DIFFERENCE with the FFS_TEMPLATE stored in the memory 14 to determine whether the true far-field signal sample (as represented by the FFS_DIFFERENCE) is approximately equal to the FFS_TEMPLATE. As was previously discussed, the FFS_TEMPLATE may be supplied by the medical practitioner using the programmer 100 or, preferably, may be automatically determined by the control system 30. The control program module described below in connection with FIG. 4 provides an advantageous technique for automatically determining the FFS_TEMPLATE.

If it is determined at the test 210 that the FFS_DIFFERENCE is approximately equal to the FFS_TEMPLATE, then at a step 212 atrial capture is deemed to have been verified, and the control program ends at a step 214. If, on the other hand, the FFS_DIFFERENCE is not approximately equal to the FFS_TEMPLATE, then at a step 216 the control system 30 performs an atrial pacing energy determination procedure. Various advantageous and appropriate atrial pacing energy determination procedures are well known in the art and will not therefore be described herein.

Figure 4:
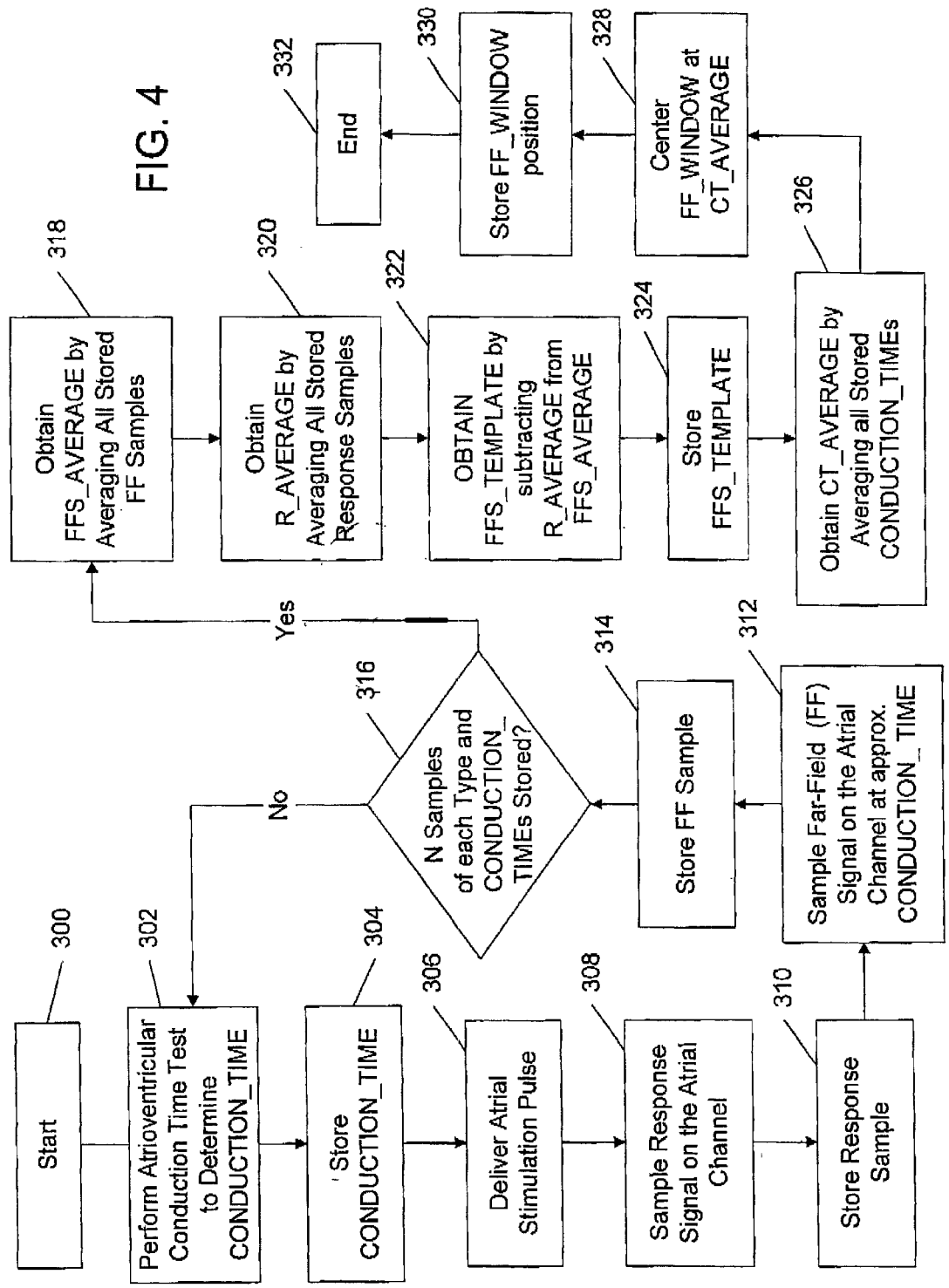
FIG. 4 is a logic flow diagram of an automatic far-field interval window and far-field signal recognition template determination program executed by the control system of the pacemaker of FIG. 1, in accordance with the principles of the present invention.

FIG. 4 depicts a logic flow diagram representing a preferred embodiment of a control program module for automatically determining the expected delay and the centering of the FFI_WINDOW at the expected delay, and for automatically determining the FFS_TEMPLATE. After the control program module begins at a step 300, the control system 30 at a step 302 performs an AV conduction test to determine the expected delay ("CONDUCTION_TIME") between the delivery of the atrial stimulation pulse and the sensing of the far-field R-wave signal by the atrial sense amplifier 26. As was previously described, the expected delay is equivalent to AV conduction time. Various advantageous and appropriate AV conduction time measurement procedures are well known in the art and will not therefore be described herein. At a step 304, the control system 30 stores the thereby determined CONDUCTION_TIME in the memory 14.

At a step 306, the control system 30 causes the atrial pulse generator 16 to deliver a stimulation pulse to the atrial chamber of the heart 24. When delivered, the atrial stimulation pulse triggers a response signal in the atrial chamber that may consist of an evoked response representative of an atrial contraction combined with a polarization signal. Typically, the atrial stimulation pulse also triggers a subsequent ventricular contraction resulting in a ventricular R-wave that is sensed by the atrial channel amplifier 26 through the atrial lead 32 as a far-field signal.

At a step 308, the control system 30 samples the response signal via the sampler 36, and at a step 310 stores the response sample in the memory 14. At a step 312, the control system 30 samples the far-field signal via the sampler 36 after a delay, following the delivery of the atrial stimulation pulse at the step 306, approximately equal to the CONDUCTION_TIME. At a step 314, the control system 30 stores the far-field signal sample in the memory 14.

At a test 316, the control system 30 determines whether a predetermined number (hereinafter "N") of each of the response samples, far-field signal samples, and CONDUCTION_TIMEs are stored in the memory 14. The parameter N may be selected by the medical practitioner using the programmer 100. In order to increase precision of the FF_WINDOW positioning and to improve the accuracy of the FFS_TEMPLATE, N should be set to a sufficient number of samples to accurately classify the conduction time (e.g., three samples or more).

If N CONDUCTION_TIMES and samples of each type have not been stored, then the control system 30 returns from the step 316 to the step 302 to perform the AV conduction test. Thus, the control system 30 repeats the steps 302 through 314 until N CONDUCTION_TIMEs and N samples of each type have been stored in the memory 14. When N CONDUCTION_TIMEs and N samples of each type have been stored, at a step 318 the control system 30 determines a FFS_AVERAGE representative of an average far-field signal sample by averaging all of the stored far-field signal samples, and optionally stores the FFS_AVERAGE in the memory 14. At a step 320, the control system 30 similarly determines an R_AVERAGE representative of an average response sample by averaging all of the stored response samples, and optionally stores the calculated R_AVERAGE in the memory 14.

At a step 322, the control system 30 determines the FFS_TEMPLATE representative of a true far-field signal by subtracting R_AVERAGE from FFS_AVERAGE. Because FFS_AVERAGE represents the average far-field signal whereas the raw detected far-field signal may be mixed with the response signal, subtracting the R_AVERAGE (representative of just the response signal including polarization and other noise) from the FFS_AVERAGE results in a representation of the true far-field signal. At a step 324, the FFS_TEMPLATE is stored in the memory 14, so that it is available for future identification of a far-field signal during atrial capture verification as described above in connection with FIGS. 2–3.

At a step 326, the control system 30 determines an average expected delay value CT_AVERAGE by averaging all CONDUCTION_TIMEs stored in the memory 14 and, at a step 328, centers the predefined FF_WINDOW at the CT_AVERAGE. At a step 330, the control system 30 stores the FF_WINDOW position to increase the capability of the atrial channel amplifier 26 to sense far-field signals that occur before or after the expected delay, and then ends the control program module at a step 332.

To further improve the accuracy of the CT_AVERAGE determination and the clarity of the FFS_TEMPLATE in systems using bipolar pacing, the sensing polarity may be designated by the physician and automatic electrode polarity switching enabled.

Referring now to FIGS. 5 and 6, an alternative stimulation device 10 capable of utilizing the present invention will be described. FIG. 5 illustrates the stimulation device 10 in electrical communication with a patient's heart 24 by way of three leads 420, 424 and 430 suitable for delivering multi-chamber stimulation and shock therapy. To sense atrial cardiac signals and to provide right atrial chamber stimulation therapy, the stimulation device 10 is coupled to an implantable right atrial lead 420 having at least an atrial tip electrode 422, which typically is implanted in the patient's right atrial appendage.

To sense left atrial and ventricular cardiac signals and to provide left-chamber pacing therapy, the stimulation device 10 is coupled to a "coronary sinus" lead 424 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 424 is designed to receive atrial and ventricular cardiac signals and to deliver: left ventricular pacing therapy using at least a left ventricular tip electrode 426, left atrial pacing therapy using at least a left atrial ring electrode 427, and shocking therapy using at least a left atrial coil electrode 428. For a complete description of a coronary sinus lead, refer to U.S. patent application Ser. No. 09/457,277 filed Dec. 8, 1999, entitled "A Self-Anchoring, Steerable Coronary Sinus Lead (Pianca et al.), which is a continuation-in-part of U.S. patent application Ser. No. 09/196,898, filed Nov. 20, 1998, now abandoned; and U.S. Pat. No. 5,466,254, titled "Coronary Sinus Lead with Atrial Sensing Capability" (Helland), which patents are hereby incorporated herein by reference.

The stimulation device 10 is also shown in electrical communication with the patient's heart 24 by way of an implantable right ventricular lead 430 having, in this embodiment, a right ventricular tip electrode 432, a right ventricular ring electrode 434, a right ventricular (RV) coil electrode 436, and an SVC coil electrode 438. Typically, the right ventricular lead 430 is transvenously inserted into the heart 24 so as to place the right ventricular tip electrode 432 in the right ventricular apex so that the RV coil electrode 436 will be positioned in the right ventricle and the SVC coil electrode 438 will be positioned in the superior vena cava. Accordingly, the right ventricular lead 430 is capable of receiving cardiac signals, and delivering stimulation in the form of pacing and shock therapy to the right ventricle.

FIG. 6 illustrates a simplified block diagram of the multi-chamber implantable stimulation device 10, which is capable of treating both fast and slow arrhythmias with stimulation therapy, including pacing stimulation, cardioversion, and defibrillation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 is encased in a housing 440 which is often referred to as "can", "case" or "case electrode", and which may be programmably selected to act as the return electrode for all "unipolar" pacing or sensing modes.

Device 10 generally includes an atrial channel, which includes atrial sensing circuitry 482 and an atrial pulse generator 470, and a ventricular channel, which includes ventricular sensing circuitry 484 and a ventricular pulse generator 472. Interpretation of sensed atrial and ventricular activity and coordination of pacing, cardioversion, or defibrillation therapy delivery by the atrial and ventricular channels are controlled by the programmable microcontroller 460.

The microcontroller 460 typically includes a microprocessor and memory such that operation codes can be performed based on programmable parameters, such as pacing pulse amplitude, AV interval, sensitivity and so forth. Such programmable parameters may be selected by the physician using an external device 502 in communication with a telemetry circuit 500.

In this embodiment, the control program is comprised of multiple integrated program modules, with each module bearing responsibility for controlling one or more functions of the stimulation device 10. For example, one program module may control the delivery of stimulating pulses to the heart 24, while another may control the ventricular pacing energy determination. In effect, each program module is a control program dedicated to a specific function or set of functions of the stimulation device 10.

Referring to FIG. 6, the housing 440, encasing the multi-chamber implantable stimulation device 10 includes a connector (not shown) having a plurality of terminals, 442, 444, 446, 448, 452, 454, 456, and 458 that are shown schematically and, for convenience, the names of the electrodes to which they are connected are shown next to the terminals. As such, to achieve right atrial sensing and pacing, the connector includes at least a right atrial tip terminal 442 adapted for connection to the atrial (AR) tip electrode 422.

To achieve left chamber sensing, pacing or shocking, the connector includes at least a left ventricular ($V_L$) tip terminal 444, a left atrial ($A_L$) ring terminal 446, and a left atrial ($A_L$) shocking terminal 448, which are adapted for connection to the left ventricular tip electrode 426, the left atrial tip electrode 427, and the left atrial coil electrode 428, respectively.

To support right chamber sensing, pacing and/or shocking, the connector further includes a right ventricular ($V_R$) tip terminal 452, a right ventricular ($V_R$) ring terminal 454, a right ventricular ($R_V$) shocking terminal 456, and an SVC shocking terminal 458, which are adapted for connection to the right ventricular tip electrode 432, right ventricular ring electrode 434, the RV coil electrode 436, and the SVC coil electrode 438, respectively.

At the core of the stimulation device 10 is the programmable microcontroller 460 that controls the various modes of stimulation therapy. The microcontroller 460 typically includes a microprocessor, or equivalent control circuitry, designed specifically for controlling the delivery of stimulation therapy, and may further include RAM or ROM memory, logic and timing circuitry, state machine circuitry, and I/O circuitry.

The microcontroller 460 has the ability to process or monitor input signals (data) as controlled by a program code stored in a designated block of memory. The details of the design and operation of the microcontroller 460 are not critical to the present invention. Rather, any suitable microcontroller 460 may be used that carries out the functions described herein. The use of microprocessor-based control circuits for performing timing and data analysis functions are well known in the art. Representative types of control circuitry that may be used with the present invention include the microprocessor-based control system of U.S. Pat. No. 4,940,052 (Mann et. al), and the state-machine of U.S. Pat. Nos. 4,712,555 (Sholder) and 4,944,298 (Sholder).

As shown in FIG. 6, an atrial pulse generator 470 and a ventricular pulse generator 472 generate pacing stimulation pulses for delivery by the right atrial lead 420, the right ventricular lead 430, and/or the coronary sinus lead 424 via the switch bank 474. It is understood that in order to provide stimulation therapy in each of the four chambers of the heart, the atrial pulse generator 470 and the ventricular pulse generator 472 may include dedicated, independent pulse generators, multiplexed pulse generators, or shared pulse generators. The atrial pulse generator 470 and the ventricular pulse generator 472 are controlled by the microcontroller 460 via appropriate control signals 476 and 478, respectively, to trigger or inhibit the stimulation pulses.

The microcontroller 460 further includes timing control circuitry 479 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

Atrial sensing circuits 482 and ventricular sensing circuits 484 may also be selectively coupled to the right atrial lead 420, coronary sinus lead 424, and the right ventricular lead 430, through the switch bank 474, for detecting the presence of cardiac activity in each of the four chambers of the heart. Accordingly, the atrial and ventricular sensing circuits 482 and 484 may include dedicated sense amplifiers, multiplexed amplifiers, or shared amplifiers. The switch bank 474 determines the "sensing polarity" of the cardiac signal by selectively closing the appropriate switches. In this way, the clinician may program the sensing polarity independent of the stimulation polarity. In accordance with the present invention, the polarity for sensing the ventricular EGM during capture verification and the polarity for sensing the atrial EGM during fusion detection can be programmably selected.

Each of the atrial sensing circuit 482 or the ventricular sensing circuit 484 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

For a more complete description of a typical sensing circuit, refer to U.S. Pat. No. 5,573,550, titled "Implantable Stimulation Device having a Low Noise, Low Power, Precision Amplifier for Amplifying Cardiac Signals" (Zadeh et al.). For a more complete description of an automatic gain control system, refer to U.S. Pat. No. 5,685,315, titled "Cardiac Arrhythmia Detection System for an Implantable Stimulation Device" (McClure et. al). U.S. Pat. Nos. 5,573,550 and 5,685,315 are hereby incorporated herein by reference.

The outputs of the atrial and ventricular sensing circuits 482 and 484 are connected to the microcontroller 460 for pacing or inhibiting the atrial and ventricular pulse generators 470 and 472, respectively, in a demand fashion, in response to the absence or presence of cardiac activity, respectively, in the appropriate chambers of the heart. The atrial and ventricular sensing circuits 482 and 484, in turn, receive control signals over signal lines 486 and 488 from the microcontroller 460, for controlling the gain, threshold, polarization charge removal circuitry (not shown), and the timing of any blocking circuitry (not shown) coupled to the inputs of the atrial and ventricular sensing circuits 482 and 484.

For arrhythmia detection, the stimulation device 10 utilizes the atrial and ventricular sensing circuits 482 and 484 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 460 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 490. The data acquisition system 490 is configured to acquire intracardiac electrogram signals, convert the raw analog data into digital signals, and store the digital signals for later processing and/or telemetric transmission to an external device 502. The data acquisition system 490 is coupled to the right atrial lead 420, the coronary sinus lead 424, and the right ventricular lead 430 through the switch bank 474 to sample cardiac signals across any pair of desired electrodes.

Advantageously, the data acquisition system 490 may be coupled to the microcontroller 460 or another detection circuitry, for detecting an evoked response from the heart 24 in response to an applied stimulus, thereby aiding in the detection of "capture". The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing circuitry within the microcontroller 460, and enabling the data acquisition system 490 via control signal 492 to sample the cardiac signal that falls in the capture detection window and, based on the amplitude of the sampled cardiac signal, determines if capture has occurred. In accordance with the preferred embodiment of the present invention, whenever capture verification is enabled, the methods for distinguishing loss of capture from fusion as described herein are employed.

If a loss of capture in any chamber is detected during capture verification, microcontroller 460 initiates a threshold test to re-determine the capture threshold in that particular chamber. In one embodiment, a capture threshold test may also be performed on a periodic basis, such as once a day during at least the acute phase (e.g. the first 30 days) and less frequently thereafter. A threshold test would begin at a desired starting point (either a high energy level or the level at which capture is currently occurring) and decrease the energy level until capture is lost. The value at which capture is lost is known as the capture threshold. Thereafter, the pacing pulse energy is adjusted to the capture threshold plus some safety margin.

The methods of the present invention for detecting and avoiding fusion may be applied during threshold testing such that pacing output is not driven to a maximum level due to fusion events precluding capture recognition.

The microcontroller 460 is coupled to a memory 494 by a suitable data/address bus 496, wherein the programmable operating parameters used by the microcontroller 460 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 24 within each respective tier of therapy.

Advantageously, the operating parameters of the stimulation device 10 may be non-invasively programmed into the memory 494 through a telemetry circuit 500 in telemetric communication with the external device 502, such as a programmer, transtelephonic transceiver, or a diagnostic system analyzer. The telemetry circuit 500 is activated by the microcontroller 460 by a control signal 506. The telemetry circuit 500 advantageously allows intracardiac electrograms and status information relating to the operation of the stimulation device 10 (as contained in the microcontroller 460 or memory 494) to be sent to the external device 502 through the established communication link 504.

In one embodiment, the stimulation device 10 may further include a physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g. detecting sleep and wake states). Accordingly, the microcontroller 460 responds by adjusting the various pacing parameters (such as rate, AV Delay, V—V Delay, etc.) at which the atrial and ventricular pulse generators 470 and 472 generate stimulation pulses.

The stimulation device 10 additionally includes a power source such as a battery 510 that provides operating power to all the circuits shown in FIG. 6. For the stimulation device 10, which employs shocking therapy, the battery 510 must be capable of operating at low current drains for long periods of time and also be capable of providing high-current pulses (for capacitor charging) when the patient requires a shock pulse. The battery 510 must preferably have a predictable discharge characteristic so that elective replacement time can be detected. Accordingly, the stimulation device 10 can employ lithium/silver vanadium oxide batteries.

As further shown in FIG. 6, the stimulation device 10 is shown as having an impedance measuring circuit 512 which is enabled by the microcontroller 460 by a control signal 514. The known uses for an impedance measuring circuit 520 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; predicting the remaining battery life; measuring stroke volume; and detecting the opening of the valves, etc. The impedance measuring circuit 512 is advantageously coupled to the switch bank 474 so that any desired electrode may be used. The impedance measuring circuit 512 is not critical to the present invention and is shown for only completeness of the description.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 Joules), moderate (0.5–10 Joules), or high (11 to 40 Joules) energy, as controlled by the microcontroller 460. Such shocking pulses are applied to the patient's heart through at least two shocking electrodes, and as shown in this embodiment, selected from the left atrial coil electrode 428, the RV coil electrode 436, and/or the SVC coil electrode 438 (FIG. 5). As noted above, the housing 440 may act as an active electrode in combination with the RV electrode 436, or as part of a split electrical vector using the SVC coil electrode 438 or the left atrial coil electrode 428.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

One skilled in the art will appreciate that the present invention can be practiced by other than the described embodiments, which are presented for purposes of illustration and not of limitation.

What is claimed is:

1. A method of detecting capture in an atrial chamber, comprising:
   automatically switching an electrode polarity from a bipolar sensing configuration to a unipolar sensing configuration at an onset of a far-field interval window, for detecting a far-field signal; and
   automatically switching the electrode polarity from the unipolar sensing configuration to the bipolar sensing configuration at an end of the far-field interval window.

2. The method according to claim 1, further including delivering an atrial stimulation pulse.

3. The method according to claim 2, further including centering the far-field interval window substantially at an expiration of an expected delay between the delivery of the atrial stimulation pulse and the far-field signal.

4. The method according to claim 3, further including setting the expected delay to be approximately equal to an AV conduction time.

5. The method according to claim 4, wherein detecting the far-field signal includes detecting a far-field R-wave.

6. The method according to claim 5, wherein detecting the far-field signal includes calculating a far-field signal recognition template.

7. The method according to claim 6, further including sampling the far-field signal resulting from the delivery of the atrial stimulation pulse during the far-field interval window.

8. The method according to claim 7, further including comparing a far-field signal sample to the far-field signal recognition template to verify whether a morphology of the far-field signal sample corresponds to the far-field R-wave that is expected to follow a successfully captured atrial stimulation pulse.

9. The method according to claim 8, wherein if the far-field signal sample is approximately equal to the far-field signal recognition template, then atrial capture is deemed verified.

10. The method according to claim 9, wherein if the far-field signal sample does not correspond to the far-field signal recognition template, then performing an atrial stimulation energy determination procedure.

11. A device for detecting capture in an atrial chamber, comprising:
    an electrode designed to be implanted in the atrial chamber;
    a control system including a switching circuit which is electrically connected to the electrode, in order to automatically switch a polarity of the electrode from a bipolar sensing configuration to a unipolar sensing configuration at an onset of a far-field interval window, for detecting a far-field signal; and
    the switching circuit automatically switching the electrode polarity from the unipolar sensing configuration to the bipolar sensing configuration at an end of the far-field interval window.

12. The device according to claim 11, further including a pulse generator that delivers an atrial stimulation pulse.

13. The device according to claim 12, wherein the far-field interval window is substantially centered at an expiration of an expected delay between the delivery of the atrial stimulation pulse and the far-field signal.

14. The device according to claim 13, wherein the expected delay is approximately equal to an AV conduction time.

15. The device according to claim 14, wherein the far-field signal includes a far-field R-wave.

16. The device according to claim 15, wherein the control system detects the far-field signal by calculating a far-field signal recognition template.

17. The device according to claim 16, wherein the control system includes a sampler that samples the far-field signal resulting from the delivery of the atrial stimulation pulse during the far-field interval window.

18. The device according to claim 17, wherein the control system compares a far-field signal sample to the far-field signal recognition template, to determine whether a morphology of the far-field signal sample corresponds to the far-field R-wave that is expected to follow a successfully captured atrial stimulation pulse.

19. The device according to claim 18, wherein the control system verifies atrial capture if the far-field signal sample is approximately equal to the far-field signal recognition template.

20. The device according to claim 19, wherein the control system performs an atrial stimulation energy determination procedure if the far-field signal sample does not correspond to the far-field signal recognition template.

21. A device for detecting capture in an atrial chamber, comprising:

an electrode designed to be implanted in the atrial chamber;

a control program implemented by a control system that is electrically connected to the electrode, to automatically switch a polarity of the electrode from a bipolar sensing configuration to a unipolar sensing configuration at an onset of a far-field interval window, for detecting a far-field signal; and the control program automatically switching the electrode polarity from the unipolar sensing configuration to the bipolar sensing configuration at an end of the far-field interval window.

22. A method of detecting capture in an atrial chamber, comprising:

automatically switching an electrode polarity from a stimulation configuration to a sensing configuration at an onset of a far-field interval window, for detecting a far-field signal; and automatically switching the electrode polarity from the sensing configuration to the stimulation configuration at an end of the far-field interval window.

* * * * *